United States Patent
Kim et al.

(10) Patent No.: US 10,820,613 B2
(45) Date of Patent: Nov. 3, 2020

(54) PLASMA STERILIZER APPARATUS FOR PIPE

(71) Applicant: KOREA FOOD RESEARCH INSTITUTE, Jeollabuk-do (KR)

(72) Inventors: Yunji Kim, Seongnam-si (KR); Eunjung Lee, Seongnam-si (KR); Okkyung Koo, Seongnam-si (KR); Hyunjoo Chang, Yongin-si (KR); Joosung Kim, Yongin-si (KR)

(73) Assignee: KOREA FOOD RESEARCH INSTITUTE, Jeollabuk-do (KR)

( * ) Notice: Subject to any disclaimer, the term of this patent is extended or adjusted under 35 U.S.C. 154(b) by 142 days.

(21) Appl. No.: 15/754,145

(22) PCT Filed: Nov. 16, 2015

(86) PCT No.: PCT/KR2015/012272
§ 371 (c)(1),
(2) Date: Feb. 21, 2018

(87) PCT Pub. No.: WO2017/034082
PCT Pub. Date: Mar. 2, 2017

(65) Prior Publication Data
US 2018/0249737 A1    Sep. 6, 2018

(30) Foreign Application Priority Data

Aug. 24, 2015 (KR) .................. 10-2015-0118637

(51) Int. Cl.
*A23L 3/26* (2006.01)
*A61L 2/14* (2006.01)
(Continued)

(52) U.S. Cl.
CPC ............ *A23L 3/26* (2013.01); *A23B 7/015* (2013.01); *A23L 3/32* (2013.01); *A61L 2/14* (2013.01);
(Continued)

(58) Field of Classification Search
CPC ...... A23L 3/26; A23L 3/32; A61L 2/14; C02F 1/467; C02F 1/46109; C02F 2201/46105;
(Continued)

(56) References Cited

FOREIGN PATENT DOCUMENTS

GB           696060    *  8/1953
KR      10-0807679 B1     2/2008
(Continued)

*Primary Examiner* — Xiuyu Tai
(74) *Attorney, Agent, or Firm* — Novick, Kim & Lee, PLLC; Jae Youn Kim; Jihun Kim (57) ABSTRACT

Disclosed is a plasma sterilizer apparatus for a pipe and, more particularly, to a plasma sterilizer apparatus for a pipe, which can be easily mounted on a pipe and effectively sterilize harmful microorganisms contained in water or raw materials flowing through a pipe. A plasma sterilizer apparatus for a pipe comprises: a first connection member connected to one side of a pipe; a second connection member connected to the other side of the pipe; a first electrode mounting member disposed in contact with the first connection member; a second electrode mounting member disposed in contact with the second connecting member; a first electrode member provided on the first electrode mounting member; and a second electrode member provided on the second electrode mounting member.

4 Claims, 8 Drawing Sheets (51) Int. Cl.
    *A23L 3/32*     (2006.01)
    *A23B 7/015*     (2006.01)
    *C02F 1/46*     (2006.01)
    *C02F 1/467*     (2006.01)
    *C02F 1/461*     (2006.01)

(52) U.S. Cl.
    CPC ............ C02F 1/467 (2013.01); C02F 1/4608 (2013.01); *C02F 1/46109* (2013.01); *C02F 2201/46105* (2013.01); *C02F 2303/04* (2013.01); *C02F 2305/023* (2013.01)

(58) Field of Classification Search
    CPC ................ C02F 2303/04; C02F 1/4608; C02F 2305/023; C02F 1/46104; C02F 2201/003; C02F 2001/46157; C02F 2201/46125; C02F 2201/4611; C02F 2303/22; C02F 2001/46138; A23B 7/015
    See application file for complete search history.

(56) References Cited

FOREIGN PATENT DOCUMENTS

| | | |
|---|---|---|
| KR | 10-1057123 B1 | 8/2011 |
| KR | 10-2013-0117598 A | 10/2013 |
| KR | 10-2014-0018158 A | 2/2014 |
| KR | 10-2015-0094170 A | 8/2015 |

* cited by examiner

PLASMA STERILIZER APPARATUS FOR PIPE

TECHNICAL FIELD

The present invention relates to a plasma sterilizer apparatus for pipe, which is easily mounted on the pipe and effectively sterilize harmful microorganisms contained in water or raw materials flowing through the pipe.

BACKGROUND ART

A sterilization process is needed to eliminate harmful microorganisms in water or raw materials in a process of making food or filtering water, and made in physical and chemical methods.

As the physical method, there are dry heat sterilization, high pressure steam sterilization, intermittent sterilization, and UV or radiation sterilization those sterilize the harmful microorganisms with high temperature or high pressure for long time.

Thus, the physical sterilization method needs very long processing time to make the condition in high temperature or high pressure, and much cost for some machine to make the condition.

The chemical sterilization method causes harmful influence to human body and environmental pollution because it uses toxic substances such like specific germicide and disinfectant gas to get rid of bacteria.

In particular, the physical or chemical sterilization method causes various problems below in the process of making food such like Kimchi.

The main ingredients of Kimchi are vegetables grown in the soil, and harmful microorganisms from the soil would remain on the vegetables. If the harmful microorganisms are sterilized in high temperature by physical method, the ingredients would not be used to make the Kimchi. Also, if the sterilization is performed with chemicals such as chlorine by the chemical method, the marketability of the Kimchi falls off because of the residue of unpleasant smell on Kimchi.

Recently, UV sterilizer is used more than the physical or chemical sterilization method, but it has the limit of low sterilization effect. Besides, a method of ozone sterilization is proposed, but ozonize treatment has problem of causing air pollution in low concentration, and threatening human health on eyes or respiratory organs.

As a counterplan for the prior sterilization method, fast and cheap plasma sterilization is proposed. However, it is difficult to install the component of a plasma generating device such like an electrode in a water pipe or food manufacturing vessel, and it lacks of operational stability and safety so as not to be used substantially.

DETAILED DESCRIPTION OF THE INVENTION

Technical Problem

The present invention is suggested to overcome the aforementioned problem and aims to provide a plasma sterilizer apparatus to install easily in pipe and sterilize the harmful microorganisms in the water or raw substances flow through the pipe effectively.

Technical Solution

To achieve the object above, the plasma sterilizer apparatus on pipe according to an aspect of the present invention comprises: a first connection member connected to one side of a pipe, a second connection member connected to the other side of a pipe, a first electrode member installed in the first connection member, and a second electrode member installed in the second connection member.

Herein, the first and the second electrode member might comprise a plane electrode of mesh structure which is woven with conductive linear members, and an electrode wire which is extended from the plane electrode to an external power line. And, the first connection member might comprises a first connection body which is connected to the pipe of the one side, and a first electrode member mounting part which is formed on the first connection body to install the first electrode member, and the second connection member comprises a second connection body which is connected to the pipe of the other side, and a second electrode member mounting part which is formed on the second connection body to install the second electrode member. In addition, the first electrode member mounting part comprises a first seating groove where the first electrode member is installed and which is grooved in a first install body extended from and formed in the first connection body, a first electrode lead-in part which protrudes from the first install body and where a lead-out hole is formed to lead the electrode wire of the first electrode member out, and a first sealing cover which is installed at the first electrode lead-in part. Or, the second electrode member mounting part comprises a second seating groove where the second electrode member is installed and which is grooved in a second install body extended from and formed in the second connection body, a second electrode lead-in part which protrudes from the second install body and where a lead-out hole is formed to lead the electrode wire of the second electrode member out, and a second sealing cover which is installed at the second electrode lead-in part. Also, a first electrode supporting member to support the first electrode member that is inserted in the first seating groove; and a second electrode supporting member to support the second electrode member that is inserted in the second seating groove are further comprised.

Meanwhile, to achieve the object, the plasma sterilizer apparatus on pipe according to another aspect of the present invention comprises a first connection member connected to one side of a pipe, a second connection member connected to the other side of a pipe, a first electrode mounting member installed in contact with the first connection member, a second electrode mounting member installed in contact with the second connection member, a first electrode member installed in the first electrode mounting member, and a second electrode member installed in the second electrode mounting member.

Herein, the first electrode mounting member might be comprised of a first install body which is circular and planar in shape with center-hollowed part; a first seating groove which is grooved to install the first electrode member on one surface of the first install body; a first electrode lead-in part which protrudes out of the first install body and has a first lead-out hole where an electrode wire of the first electrode member leads out through; and a first sealing cover 84 which is installed on the first electrode lead-in part. Also, the second electrode mounting member is comprised of a second install body which is circular and planar in shape with center-hollowed part; a second seating groove which is grooved to install the second electrode member on the second install body; a second electrode lead-in part which protrudes out of the second install body and has a second lead-out hole which an electrode wire of the second electrode member leads out through; and a second sealing cover is installed on the second electrode lead-in part.

In addition, the plasma sterilizer apparatus on pipe further comprises an interval adjusting member to adjust distance between the first and second electrode mounting members.

The first and second electrode mounting members make the plurality of pairs and the interval adjusting member are interposed between the first and second electrode mounting members for all the pairs.

Furthermore, sealing member inserting hole is grooved and formed on the inner surface of the first connection member and the inner surface of the second connection member and the inner surface of the interval adjusting member those face each other, and a sealing member is inserted in the sealing member inserting hole.

Meanwhile, a locking member to connect the first connection member and the second connection member.

Also, the first and second connection bodies comprise a flange with multiple locking holes formed in circumferential direction, and the locking member comprises bolts inserted in the locking holes and nuts fastened with the bolts.

Effects of the Invention

The plasma sterilizer apparatus is easily implemented by connecting the first and second connection members with the pipe according to the present invention so as to enhance the convenience of the use and the simplicity of the maintenance and repair.

In addition, the plasma sterilization apparatus on pipe of the present invention has superior sterilizing effect because the first and second electrode members of mesh structure are uniformly exposed to water or food materials flowing through the pipe and thus the sterilization is uniformly acted by the hydroxyl group.

Also, according to the plasma sterilization apparatus on pipe of the present invention, as the first and second electrode members can be repeatedly arranged to make a plurality of pairs, the sterilizing action or the neutralization and removal of toxic substances are performed in multiple stages. Accordingly, it is possible to effectively sterilize harmful microorganisms and effectively perform the neutralization and elimination of toxic substances even if the flow rate is fast.

BEST MODE FOR CARRYING OUT THE INVENTION

Hereinafter, the exemplary embodiments of the present invention will be described in detail referring to the appended drawings.

Figure 1:
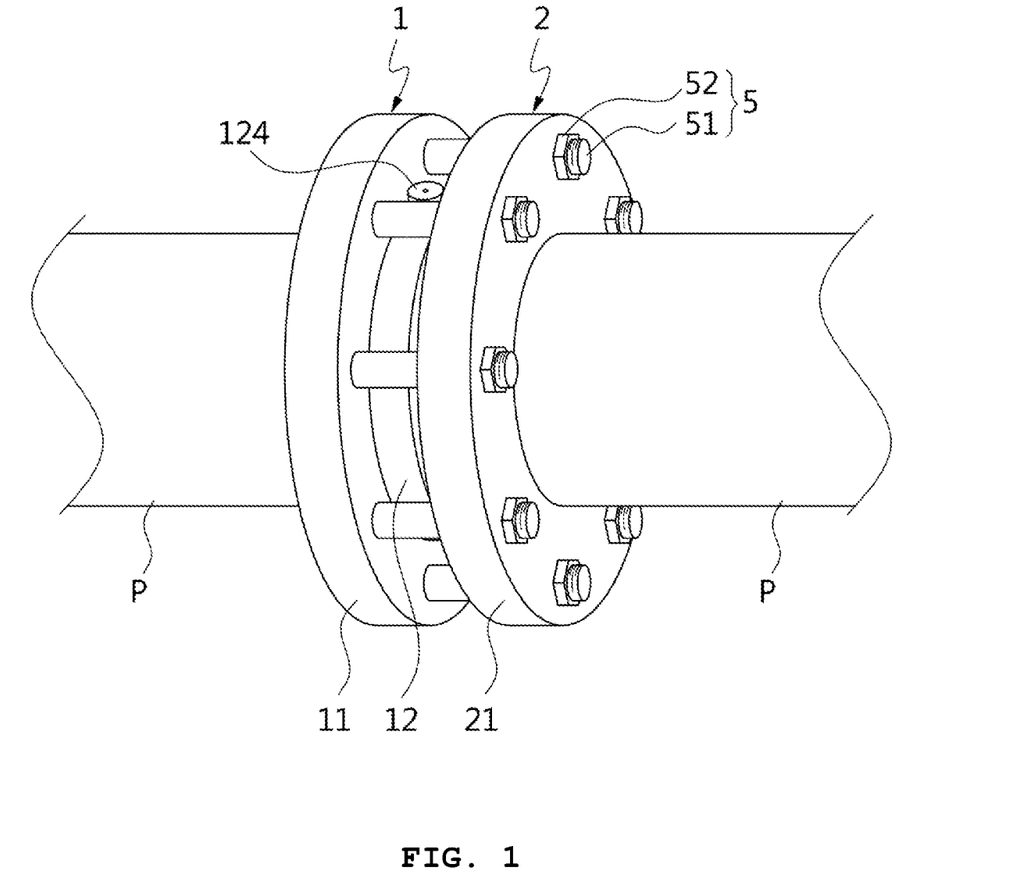
FIG. 1 is a perspective view in the assembled state of the plasma sterilization apparatus on pipe according to a first embodiment of the present invention.
Figure 2:
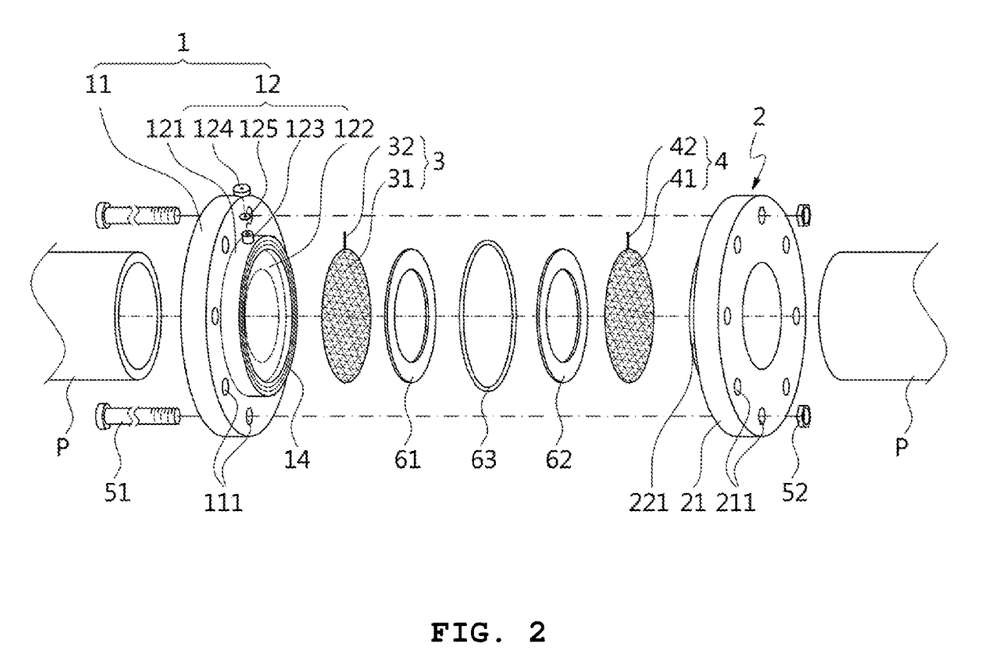
FIG. 2 is a perspective view in the separated state of the plasma sterilization apparatus on pipe according to the first embodiment of the present invention.
Figure 3:
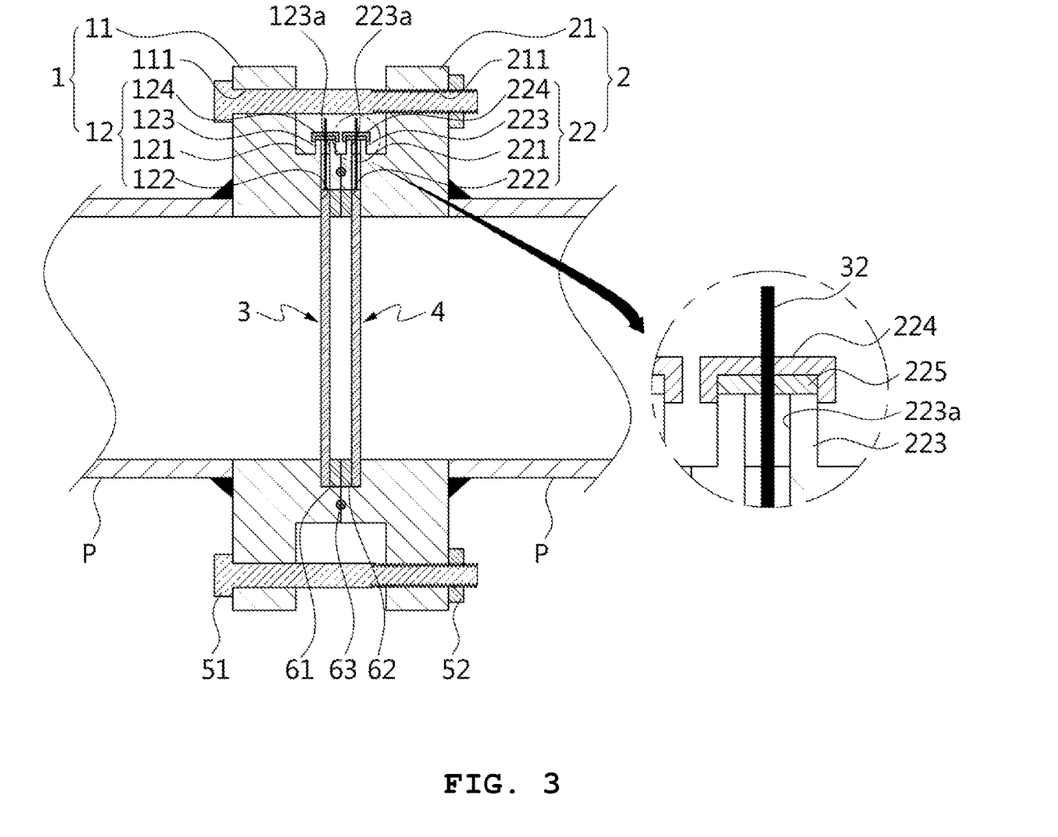
FIG. 3 is a sectional drawing of the plasma sterilization apparatus on pipe according to the first embodiment of the present invention.

FIG. 1 is a perspective view in the assembled state of the plasma sterilization apparatus on pipe according to a first embodiment of the present invention, FIG. 2 is a perspective view in the separated state of the plasma sterilization apparatus on pipe according to the first embodiment of the present invention and FIG. 3 is a sectional drawing of the plasma sterilization apparatus on pipe according to the first embodiment of the present invention.

Referring to FIG. 1 to FIG. 3, the plasma sterilizer apparatus on pipe according to the first embodiment of the present invention is installed on the pipe P and generates cold temperature plasma to sterilize, neutralize and remove the harmful materials on the fluid and food material flow through the pipe. It comprises a first connection member 1, a second connection member 2, a first electrode member 3, a second electrode member 4, and a locking member 5.

The first connection member 1 is a component connected to one side of the pipe by the connecting ways such as welding, and comprised of a first connection body 11 of a circular planar shape with center-hollowed part, and a first electrode member mounting part 12 which is formed at the first connection body 11 and where the first electrode member 3 is installed.

In addition, the first connection body 11 has multiple locking holes 111 formed in circumferential direction, similar to the mechanical component normally called a flange.

The first electrode member mounting part 12 is comprised of a first install body 121, a first seating groove 122, a first electrode lead-in part 123, and a first sealing cover 124. The first install body 121 is circular and planar in shape with center-hollowed part and extends from the first connection body 11 with forming one body with the first connection body 11. The first seating groove 122 is grooved to install the first electrode member 3 on the first install body 121. The first electrode lead-in part 123 protrudes out of the first install body 121 and has a first lead-out hole 123a which an electrode wire 32 of the first electrode member 3 leads out through. The first sealing cover 124 is installed on the first electrode lead-in part 123.

The second connection member 2 is a component connected to the other side of the pipe P by the connecting ways such as welding and comprises a second connection body 21 and a second electrode member mounting part 22 to be structurally symmetric to the first connection member 1. The second electrode member mounting part 22 is comprised of a second install body 221, a second seating groove 222, a second electrode lead-in part 223, and a second sealing cover 224. The second install body 221 is circular and planar in shape with center-hollowed part and extends from the second connection body 21 with forming one body with the first connection body 21. The second seating groove 222 is grooved to install the second electrode member 4 on the second install body 221. The second electrode lead-in part 223 has a second lead-out hole 223a which an electrode wire 42 of the second electrode member 4 leads out through. The second sealing cover 224 is installed on the second electrode lead-in part 223.

In addition, the aforementioned first and second electrode lead-in parts 123, 223 are protruded parts of the first and second install body 121,221 which have the male crew thread on the outer surface. The first and second sealing covers 124, 224 are parts of a cap in shape with a female screw thread on the inner surface, and have O-ring 125,225 inside to keep sealing.

The first electrode member 3 is a component to be installed in the first seating groove 122 of the first connection member 1 and connected with the positive power line linked to the cold plasma driving part (not shown) installed outside. It is comprised of a plane electrode 31 of mesh structure woven with conductive linear members and an electrode wire 32 connecting the plane electrode 31 with the positive power line. Herein, the conductive linear members might be a wire made of titanium alloy.

The second electrode member 4 is a component formed in same shape with the first electrode member 3 and installed in the second seating groove 222 of the second connection member 2. An electrode line 42 is connected with the negative power line (not shown) linked to the cold plasma driving part.

Also, a first electrode supporting member 61 of circular and planar shape with center-hollowed part is installed in the first seating groove 122. The first electrode supporting member 61 supports the first electrode member 3 not to be shaken by the pressure of the fluid and food material flowing through the pipe.

A second electrode supporting member 62 of circular and planar shape with center-hollowed part is installed in the second seating groove 222 and performs the same function with the first electrode supporting member 61.

Meanwhile, the locking member 5 is a component to bind the first connection member 1 and the second connection member 2 together, and comprises bolts 51 which are inserted in the locking holes 111, 211 formed in the circumferential direction of the first connection body 11 and the second connection body 21, and nuts 52 which are fastened with the bolts 51.

And, a sealing member inserting groove 14 is formed on the inner surface of the first connection member 1 and the inner surface of the second connection member 2 those are faced each other, to insert a sealing member 63 such like O-ring in.

The aforementioned cold plasma driving part comprises a power supply (not shown) and a drive circuit part (not shown) to provide the power from the power supply to the first and second electrode members 3, 4. Also, it might be implemented by selecting one among a plenty of the kwon cold plasma generators.

Hereinafter, the operation of the plasma sterilizer apparatus on pipe according to the first embodiment of the present invention will be described briefly.

After assembling the components as shown in FIG. 2 and connecting the first and second connection members 1, 2 on the pipe by welding as shown in FIG. 1 and FIG. 3, the fluid such as water or food material are provided through the pipe so as to flow via the first and second electrode members 3, 4.

If the cold plasma driving part operates at this state, a low voltage discharge phenomenon occurs between the first and second electrode members 3, 4, and the low voltage discharge phenomenon resolves the water molecule to generate cold plasma, hydroxyl ion OH and active species in oxygen O, $O_2$, $O_3$, $HO_2$, $H_2O_2$. Also, a hydroxyl group is generated by the chemical reaction of them in the water, and the strong oxidation of the hydroxyl group sterilizes harmful microorganisms such as virus or bacteria. Besides, the oxidation of the hydroxyl group neutralizes heavy metals and toxic substances and eliminates nitrogenous compound or sulfur oxide.

Figure 4:
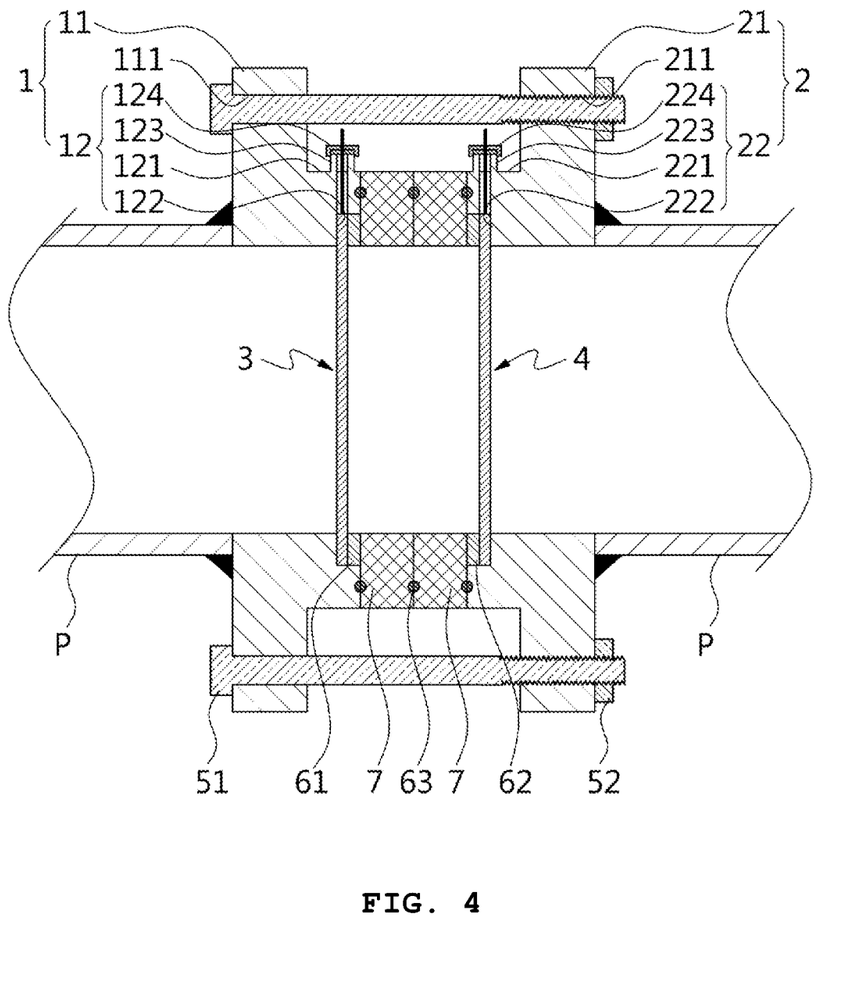
FIG. 4 is a drawing to explain an example of modification of the plasma sterilization apparatus on pipe according to the first embodiment of the present invention.

FIG. 4 is a drawing to explain an example of the modification of the plasma sterilizer apparatus on pipe according to the first embodiment of the present invention, showing sectional structure of the sterilizer in assembled state.

The plasma sterilizer apparatus on pipe according to the modified example of the first exemplary embodiment of the present invention, comprises the first connection member 1, the second connection member 2, the first electrode member 3, the second electrode member 4, and locking member 5 as shown in FIG. 2, but further comprises an interval adjusting member 7 to adjust the separation distance between the first and second electrode member 2, 3.

At least one of the interval adjusting member 7 can be arranged and have a circular and planar shape with center-hollowed part and a sealing member inserting groove on the inner surface to be inserted with sealing member 63 such like O-ring.

The aforementioned interval adjusting member 7 adjusts the separation distance between the first electrode member 3 and the second electrode member 4 based on type, amount and speed of the fluid and food material flowing through the pipe P to sterilize effectively. For example, if the amount of fluid flowing through the pipe is little, the interval adjusting member 7 will be installed to increase the separation distance between the first and second electrode member 3, 4. On the other hand, if the amount of fluid is large, the interval adjusting member 7 will be removed to make the distance between the first and second electrode member 3, 4 narrower. Thus, optimal amount of the hydroxyl group is generated according to the amount of the fluids and the uniform and stable sterilization is possible.

Mode for Embodiment of the Invention

Hereinafter, a second exemplary embodiment of the present invention will be described. Components similar with those of the aforementioned first exemplary embodiment will not be explained in detail but differential components will be explained more in detail for clarification. Also, any adoptable structure from the first exemplary embodiment can be optionally adopted to the second exemplary embodiment and detailed explanation and showing on the drawings about the adopted structure will be omitted.

Figure 5:
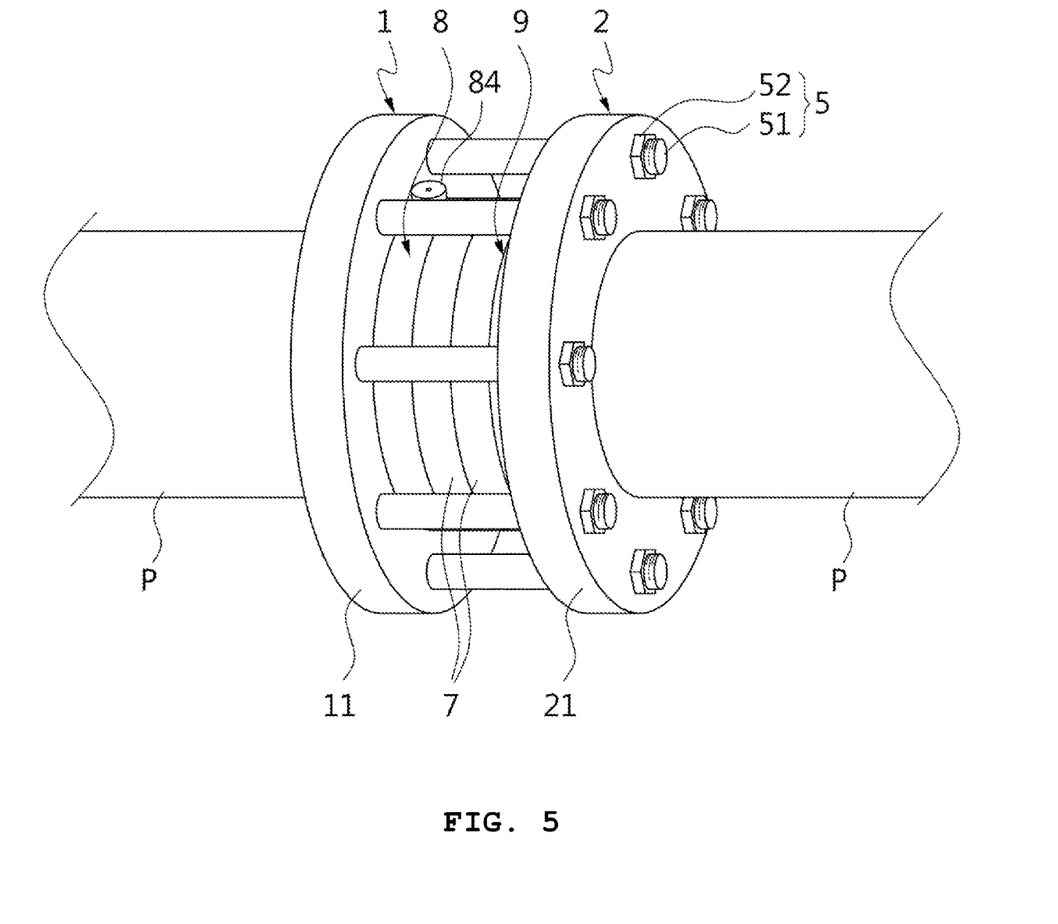
FIG. 5 is a perspective view in the assembled state of the plasma sterilization apparatus on pipe according to a second embodiment of the present invention.
Figure 6:
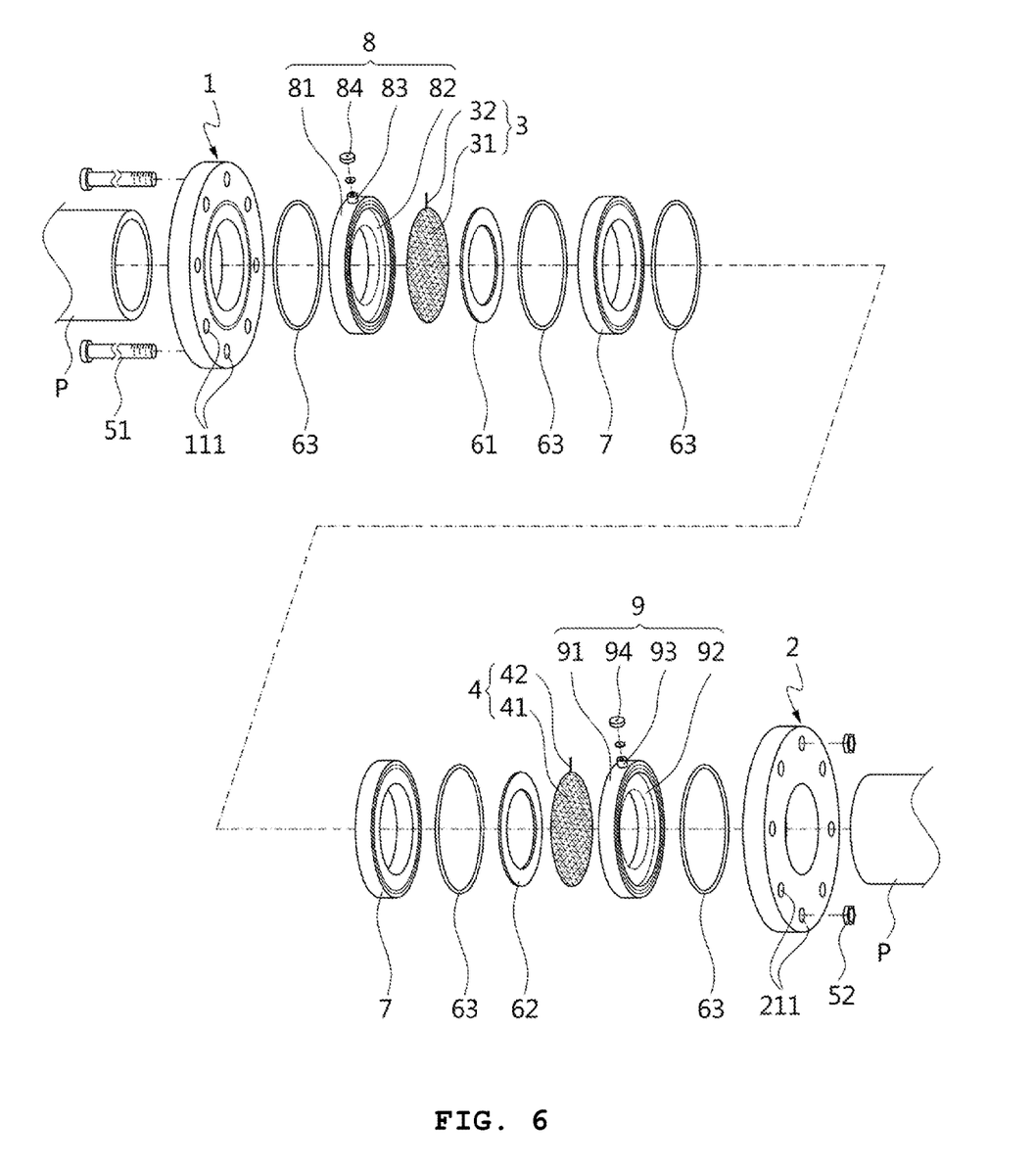
FIG. 6 is a perspective view in the separated state of the plasma sterilization apparatus on pipe according to the second embodiment of the present invention.
Figure 7:
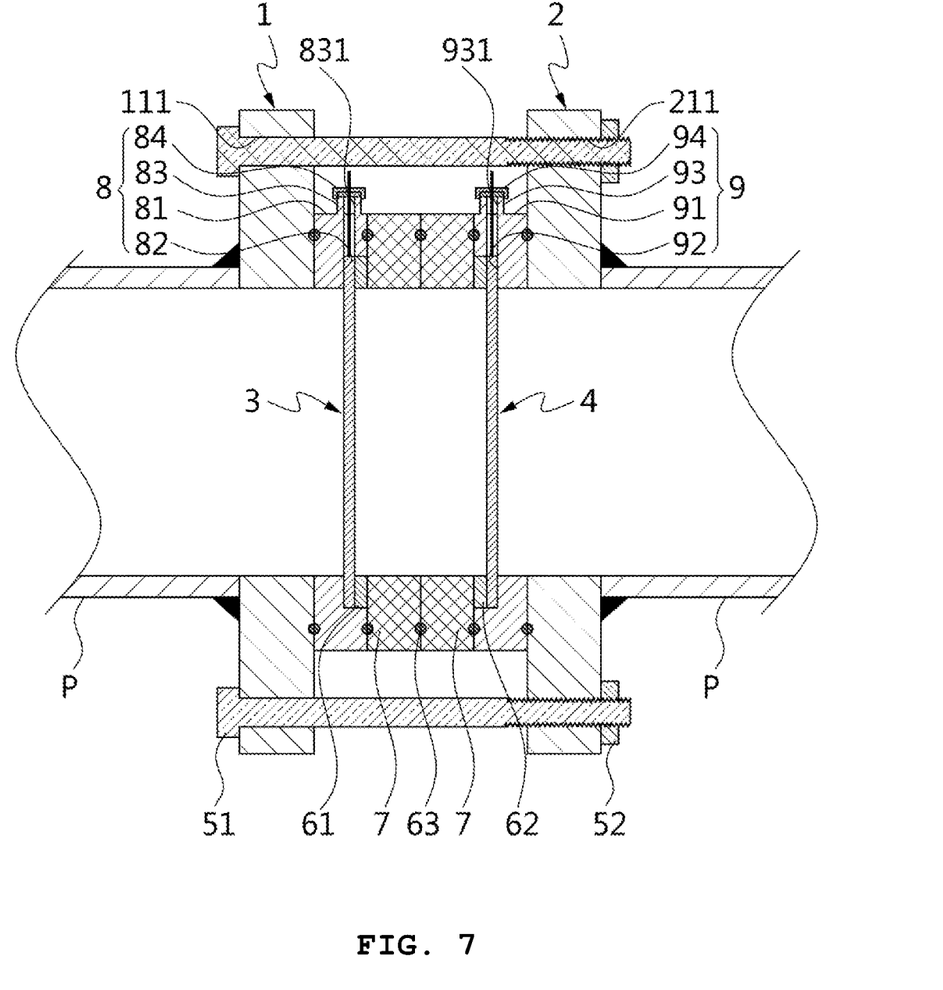
FIG. 7 is a sectional drawing of the plasma sterilization apparatus on pipe according to the second embodiment of the present invention.

FIG. 5 is a perspective view in the assembled state of the plasma sterilization apparatus on pipe according to a second embodiment of the present invention, FIG. 6 is a perspective view in the separated state of the plasma sterilization apparatus on pipe according to the second embodiment of the present invention, and FIG. 7 is a sectional drawing of the plasma sterilization apparatus on pipe according to the second embodiment of the present invention.

Referring to FIG. 5 to FIG. 7, the plasma sterilizer apparatus on pipe according to the second embodiment of the present invention generates cold plasma to perform sterilization on the fluid and food material flowing through the pipe and, and comprises the first connection member 1 connected to one side of the pipe p, the second connection member 2 connected to the other side of the pipe, the first electrode member 3, the second electrode member 4, a first electrode mounting member 8 installed close to the first connection member 1, and a second electrode mounting member 9 installed close to the second connection member 2.

The first electrode mounting member 8, where the first electrode member 3 is installed, is comprised of a first install body 81, a first seating groove 82, a first electrode lead-in part 83, and a first sealing cover 84. The first install body 81 is circular and planar in shape with center-hollowed part and the first seating groove 82 is grooved to install the first electrode member 3 on the first install body 81. The first electrode lead-in part 83 protrudes out of the first install body 81 and has a first lead-out hole 831 which an electrode wire 32 of the first electrode member 3 leads out through, and the first sealing cover 84 is installed on the first electrode lead-in part 83.

The second electrode mounting member 9, where is structurally symmetric to the first electrode mounting member 8, is comprised of a second install body 91, a second seating groove 92, a second electrode lead-in part 93, and a second sealing cover 94. The second install body 91 is circular and planar in shape with center-hollowed part and the second seating groove 92 is grooved to install the second electrode member 4 on the second install body 91. The second electrode lead-in part 93 protrudes out of the second install body 91 and has a second lead-out hole 931 which an electrode wire 42 of the second electrode member 4 leads out through, and the second sealing cover 94 is installed on the second electrode lead-in part 93.

In addition, the interval adjusting member 7 to adjust the separation distance is installed between the first and second electrode members 3, 4.

The first and second electrode member 1, 2 have multiple locking holes 111, 211 formed in circumferential direction, similar with a mechanical component normally called flange. The first electrode mounting member 8, the second electrode mounting member 9, and the interval adjusting member 7 are circular and planar in shape with a center-hollowed part.

A sealing member inserting groove is formed on the inner surface of the first connection member 1, the inner surface of the second connection member 2, the inner surface of the first electrode mounting member 8, the inner surface of the second electrode mounting member 9, and the inner surface of the interval adjusting member 7, those are faced each other, to insert a sealing member 63 such like O-ring in and keep sealing between them.

Each of the first electrode member 3 and the second electrode member 4 comprises a plane electrode 31, 41 of mesh structure which are woven with conductive linear members, and the electrode wire 32, 42 which extends from the plane electrode 31, 41 to an external power line, as mentioned above.

Figure 8:
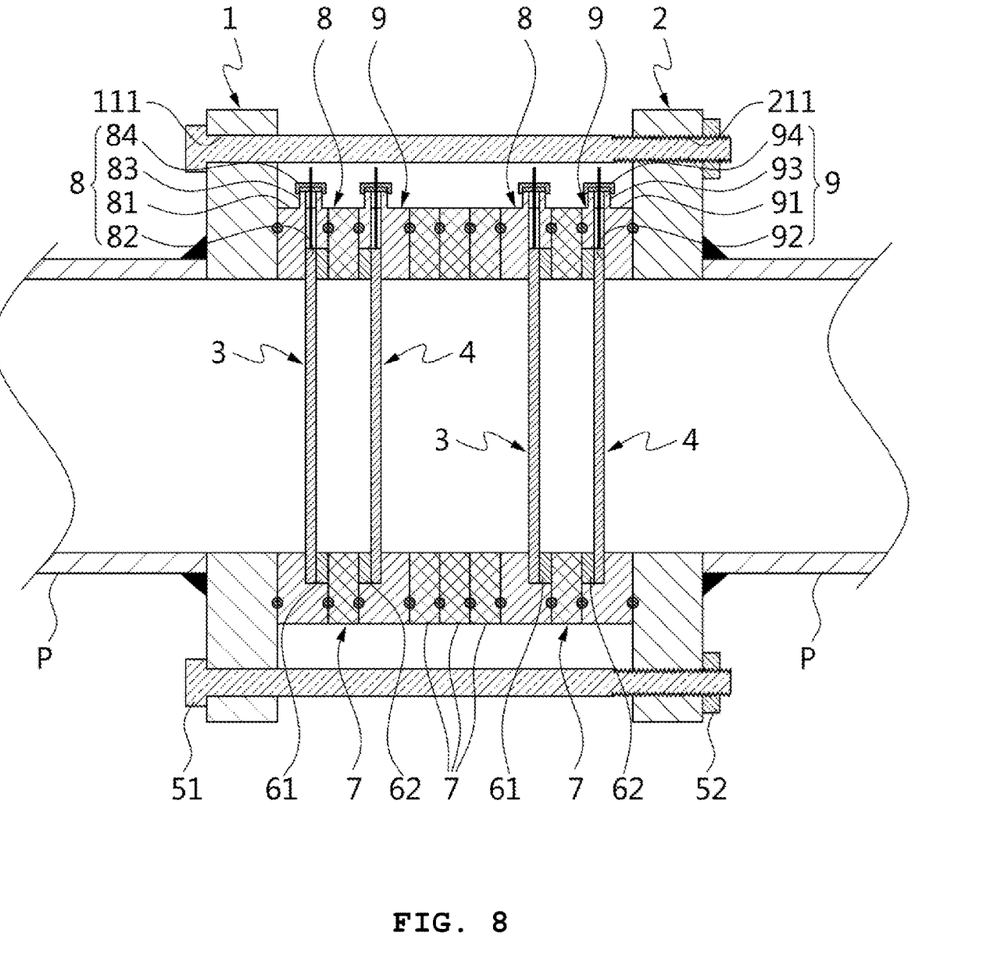
FIG. 8 is a drawing to explain an example of the modification of the plasma sterilization apparatus on pipe according to the second embodiment of the present invention.

FIG. 8 is a drawing to explain an example of the modification of the plasma sterilization apparatus on pipe according to the second embodiment of the present invention, showing sectional structure of the sterilizer in assembled state.

As shown on FIG. 8, the plasma sterilizer apparatus on pipe according to the modified example of the second exemplary embodiment of the present invention comprises the first connection member 1, the second connection member 2, the first electrode mounting member 8, the second electrode mounting member 9, the first electrode member 3, the second electrode member 4, the locking member 5, and the interval adjusting member 7. The first and second electrode mounting members 8, 9, where the first and second electrode members 3, 4 are installed, are arranged to make multiple pairs to cause low-voltage discharge in multiple stages.

Also, each of the pairs of the first and second electrode mounting members 8, 9 is intervened by the interval adjusting member 7 so as to have some separation distance.

To explain the operation of the aforementioned plasma sterilizer apparatus on pipe according to the second exemplary embodiment of the present invention briefly, the first connection member 1, the second connection member 2, the first electrode mounting member 8, the second electrode mounting member 9, the first electrode member 3, the second electrode member 4, the locking member 5, and the interval adjusting member 7 are assembled as shown in FIG. 6, are assembled in the order and the first connection member 1 and the second connection member 2 are welded on the pipe as shown in FIG. 5 and FIG. 7.

And then, if the cold plasma driving part operates at this state, a low voltage discharge phenomenon occurs between the first and second electrode members 3, 4 to generate hydroxyl group, and thus the strong oxidation of the hydroxyl group sterilizes harmful microorganisms.

In addition, to sterilize effectively is achieved by adjusting the separation distance between the first electrode member 3 and the second electrode member 4 as adjusting some parameter such like the number of the interval adjusting member 7 based on type, amount and speed of the fluid and food material flowing through the pipe P.

Especially, the plasma sterilization apparatus on pipe according to the second embodiment of the present invention has multiple pairs of the first electrode mounting member 8 and the second electrode mounting member 9, and each of them has each of the first and second electrode members 3, 4. Therefore, the sterilization and the neutralization of the toxic substances can be performed in multiple stages by multiple pairs of the first and second electrode members 3, 4. Also, even though the flowing speed is very fast, the sterilization in multiple stage can improve the sterilization effect on harmful microorganisms and the neutralization and elimination of the toxic substances effectively. In addition, there is an advantage of easy replacement and maintenance work according to the installation of the first and second electrode member 3, 4 in the first and the second electrode mounting members 8, 9 which are independent members.

The above description is just an example to perform the plasma sterilization apparatus on pipe, and it should be understood that the present invention is not limited to the exemplary embodiment and the technical idea of the present invention covers the modified scope of the present invention which those of ordinary skill in the art can modify the embodiments of the present invention.

The terms used in the exemplary embodiments have been used only to explain the exemplary embodiment, but not to make limitation on the present invention. The singular terms include plural terms if it literally has clear statement for singular term. In this patent application, the terms, such as "comprising" or "has", are to make clarification the existence of characteristics, numbers, stages, movement, components, members or the assembly of them, but not to exclude the existence or additional possibility of one or more other characteristics, numbers, stages, movements, components, members, assembly of them.

INDUSTRIAL APPLICABILITY

The plasma sterilizer apparatus on pipe according to the present invention can be used as a sterilizer in various technical fields, such like food-making or water-purifying, needing the sterilization to eliminate the harmful microorganisms included in the water or raw material.

What is claimed is:

1. A plasma sterilizer apparatus, comprising;
   a first connection member connected to a first pipe;
   a second connection member connected to a second pipe;
   a first electrode mounting member disposed in contact with the first connection member;
   a second electrode mounting member disposed in contact with the second connection member;
   a first electrode member seated on the first electrode mounting member; and
   a second electrode member seated on the second electrode mounting member,
   wherein the first electrode member comprises a first plane electrode of mesh structure which is woven with first conductive linear members, and a first electrode wire which extends from the first plane electrode to an external power line,
   wherein the second electrode member comprises a second plane electrode of mesh structure which is woven with second conductive linear members, and a second electrode wire which extends from the second plane electrode to the external power line,
   wherein the first electrode mounting member comprises a first install body which is detachable from the first connection member and has a center-hollowed circular and planar shape; a first seating groove to seat the first electrode member on one surface of the first install body; a first electrode lead-in part which protrudes from an outer surface of the first install body in a radial direction and has a first lead-out hole formed in the radial direction where the first electrode wire leads out through; and a first sealing cover which covers a distal end of the first electrode lead-in-part,
   wherein the second electrode mounting member comprises a second install body which is detachable from the second connection member and has a center-hollowed circular and planar shape; a second seating groove to seat the second electrode member on the second install body; a second electrode lead-in part which protrudes from an outer surface of the second install body in a radial direction and has a second lead-out hole formed in the radial direction where the second electrode wire leads out through; and a second sealing cover which covers a distal end of the second electrode lead-in part,
   wherein the plasma sterilizer apparatus further comprises one or more interval adjusting members disposed between the first and second electrode members to adjust a distance between the first and second electrode members,
   wherein the first connection member has a first sealing member inserting hole grooved and formed thereon, and a first sealing member is disposed in the first sealing member inserting hole to be adjacent to the first electrode mounting member,
   wherein the second connection member has a second sealing member inserting hole grooved and formed thereon, and a second sealing member is disposed in the second sealing member inserting hole to be adjacent to the second electrode mounting member, and
   wherein the plasma sterilizer apparatus further comprises a locking member to connect the first connection member and the second connection member.

2. The plasma sterilizer apparatus according to claim 1, wherein the first and second electrode mounting members, on which the first and second electrode members are respectively seated, make a plurality of pairs.

3. The plasma sterilizer apparatus according to claim 2, wherein the one or more interval adjusting members are interposed between the plurality of pairs of the first and second electrode mounting members.

4. The plasma sterilizer apparatus according to claim 1, wherein each of the first and second connection members comprises a flange on which multiple locking holes are formed in a circumferential direction thereof, and
   wherein the locking member comprises a plurality of bolts inserted in the locking holes and a plurality of nuts fastened with the plurality of bolts.

* * * * *